US010154989B2

(12) United States Patent
Kalman et al.

(10) Patent No.: US 10,154,989 B2
(45) Date of Patent: Dec. 18, 2018

(54) METHODS OF MANAGING GRAFT VERSUS HOST DISEASE (GVHD) USING INDOLE CARBOXYALDEHYDES OR DERIVATIVES THEREOF

(71) Applicant: Emory University, Atlanta, GA (US)

(72) Inventors: Daniel Kalman, Atlanta, GA (US);
Edmund K. Waller, Atlanta, GA (US);
Cynthia R. Giver, Atlanta, GA (US);
Alyson Swimm, Atlanta, GA (US);
Sravanti Rangaraju, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/268,577

(22) Filed: Sep. 17, 2016

(65) Prior Publication Data

US 2017/0079950 A1 Mar. 23, 2017

Related U.S. Application Data

(60) Provisional application No. 62/219,722, filed on Sep. 17, 2015.

(51) Int. Cl.
| | |
|---|---|
| *A01N 43/00* | (2006.01) |
| *A61K 31/33* | (2006.01) |
| *A61K 31/404* | (2006.01) |
| *A61K 45/06* | (2006.01) |

(52) U.S. Cl.
CPC ............ *A61K 31/404* (2013.01); *A61K 45/06* (2013.01)

(58) Field of Classification Search
None
See application file for complete search history.

(56) References Cited

U.S. PATENT DOCUMENTS 4,959,479 A 9/1990 Nagawa

OTHER PUBLICATIONS

Derivative. Merriam-Webster.com. Merriam-Webster, n.d. Web. Nov. 12, 2017.*
Waller et al. (2014). Administration of a Tryptophan Metabolite, Indole-3-Carboxaldehyde, Reduces Graft Versus Host Disease Morbidity and Mortality and Enhances Gastrointestinal Barrier Function in a Murine Model of Allogeneic Bone Marrow Transplantation. Blood, 124(21), 2420 Accessed Nov. 12, 2017. Retrieved.*
McSweeney et al. Bood (2001), vol. 97, pp. 3390-3400.*
Maris et al. Blood (2004), vol. 104, pp. 3535-3542.*
Bommarius et al. A Family of Indoles Regulate Virulence and Shiga Toxin Production in Pathogenic *E. coli*, PLoS ONE 8(1): e54456, 2013.
Koch et al. Inducing the tryptophan catabolic pathway, indoleamine 2,3-dioxygenase (IDO), for suppression of graft-versus-host disease (GVHD) lethality, Blood. 2009, 114(24):5062-70.
Landfried et al. Tryptophan catabolism is associated with acute GVHD after human allogeneic stem cell transplantation and indicates activation of indoleamine 2,3-dioxygenase, Blood. 2011;118(26):6971-6974.
SIGMA-ALDRICH, Indole-3-carboxaldehyde, CAS No. 487-89-8.
SIGMA-ALDRICH, Indole-3-carboxylic acid, CAS No. 771-50-6.
Soliman et al. Indoleamine 2,3-Dioxygenase: Is It an Immune Suppressor? Cancer J. 2010, 16(4):354-9.
Waller et al. Irradiated Donor Leukocytes Promote Engraftment of Allogeneic Bone Marrow in Major Histocompatibility Complex Mismatched Recipients Without Causing Graft-Versus-Host Disease, Blood, vol. 94, No. 9, 1999, 3222-3233.
Waller et al. Administration of a Tryptopha Metabolite, Indole-3-Carboxaldehyde, Reduces GVHD Morbidity and Mortality, Blood 2014 124:2420.

\* cited by examiner

*Primary Examiner* — Patrick T Lewis
(74) *Attorney, Agent, or Firm* — Emory Patent Group (57) ABSTRACT

In certain embodiments, this disclosure relates to methods of treating or preventing HvGD comprising administering an effective amount of indole-2-carboxyaldehyde, indole-3-carboxyaldehyde, or derivative to a subject in need thereof. In certain embodiments, this disclosure relates to methods of treating a subject with a hematological malignancy or other cancer comprising transplanting allogenic bone marrow or stem cells in combination with administering an effective amount of an indole-2-carboxyaldehyde, indole-3-carboxyaldehyde, or derivative thereof to a subject in need thereof.

10 Claims, 4 Drawing Sheets

FIG. 5C too long

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent. Prior to describing the various embodiments, the following definitions are provided and should be used unless otherwise indicated.

The term "subject" refers any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

The cancer to be treated in the context of the present disclosure may be any type of cancer or tumor. These tumors or cancer include, and are not limited to, tumors of the hematopoietic and lymphoid tissues or hematopoietic and lymphoid malignancies, tumors that affect the blood, bone marrow, lymph, and lymphatic system. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

Also contemplated are malignancies located in the colon, abdomen, bone, breast, digestive system, liver, pancreas, peritoneum, endocrine glands (adrenal, parathyroid, hypophysis, testicles, ovaries, thymus, thyroid), eye, head and neck, nervous system (central and peripheral), lymphatic system, pelvis, skin, soft tissue, spleen, thorax and genitourinary apparatus and, more particularly, childhood acute lymphoblastic leukemia, acute lymphoblastic leukemia, acute lymphocytic leukemia, acute myeloid leukemia, adrenocortical carcinoma, adult (primary) hepatocellular cancer, adult (primary) liver cancer, adult acute lymphocytic leukemia, adult acute myeloid leukemia, adult Hodgkin's disease, adult Hodgkin's lymphoma, adult lymphocytic leukemia, adult non-Hodgkin's lymphoma, adult primary liver cancer, adult soft tissue sarcoma, AIDS-related lymphoma, AIDS-related malignant tumors, anal cancer, astrocytoma, cancer of the biliary tract, cancer of the bladder, bone cancer, brain stem glioma, brain tumors, breast cancer, cancer of the renal pelvis and ureter, primary central nervous system lymphoma, central nervous system lymphoma, cerebellar astrocytoma, brain astrocytoma, cancer of the cervix, childhood (primary) hepatocellular cancer, childhood (primary) liver cancer, childhood acute lymphoblastic leukemia, childhood acute myeloid leukemia, childhood brain stem glioma, childhood cerebellar astrocytoma, childhood brain astrocytoma, childhood extracranial germ cell tumors, childhood Hodgkin's disease, childhood Hodgkin's lymphoma, childhood visual pathway and hypothalamic glioma, childhood lymphoblastic leukemia, childhood medulloblastoma, childhood non-Hodgkin's lymphoma, childhood supratentorial primitive neuroectodermal and pineal tumors, childhood primary liver cancer, childhood rhabdomyosarcoma, childhood soft tissue sarcoma, childhood visual pathway and hypothalamic glioma, chronic lymphocytic leukemia, chronic myeloid leukemia, cancer of the colon, cutaneous T-cell lymphoma, endocrine pancreatic islet cells carcinoma, endometrial cancer, ependymoma, epithelial cancer, cancer of the oesophagus, Ewing's sarcoma and related tumors, cancer of the exocrine pancreas, extracranial germ cell tumor, extragonadal germ cell tumor, extrahepatic biliary tract cancer, cancer of the eye, breast cancer in women, Gaucher's disease, cancer of the gallbladder, gastric cancer, gastrointestinal carcinoid tumor, gastrointestinal tumors, germ cell tumors, gestational trophoblastic tumor, tricoleukemia, head and neck cancer, hepatocellular cancer, Hodgkin's disease, Hodgkin's lymphoma, hypergammaglobulinemia, hypopharyngeal cancer, intestinal cancers, intraocular melanoma, islet cell carcinoma, islet cell pancreatic cancer, Kaposi's sarcoma, cancer of kidney, cancer of the larynx, cancer of the lip and mouth, cancer of the liver, cancer of the lung, lymphoproliferative disorders, macroglobulinemia, breast cancer in men, malignant mesothelioma, malignant thymoma, medulloblastoma, melanoma, mesothelioma, occult primary metastatic squamous neck cancer, primary metastatic squamous neck cancer, metastatic squamous neck cancer, multiple myeloma, multiple myeloma/plasmatic cell neoplasia, myelodysplastic syndrome, myelogenous leukemia, myeloid leukemia, myeloproliferative disorders, paranasal sinus and nasal cavity cancer, nasopharyngeal cancer, neuroblastoma, non-Hodgkin's lymphoma during pregnancy, non-melanoma skin cancer, non-small cell lung cancer, metastatic squamous neck cancer with occult primary, buccopharyngeal cancer, malignant fibrous histiocytoma, malignant fibrous osteosarcoma/histiocytoma of the bone, epithelial ovarian cancer, ovarian germ cell tumor, ovarian low malignant potential tumor, pancreatic cancer, paraproteinemias, purpura, parathyroid cancer, cancer of the penis, phaeochromocytoma, hypophysis tumor, neoplasia of plasmatic cells/multiple myeloma, primary central nervous system lymphoma, primary liver cancer, prostate cancer, rectal cancer, renal cell cancer, cancer of the renal pelvis and ureter, retinoblastoma, rhabdomyosarcoma, cancer of the salivary glands, sarcoidosis, sarcomas, skin cancer, small cell lung cancer, small intestine cancer, soft tissue sarcoma, squamous neck cancer, stomach cancer, pineal and supratentorial primitive neuroectodermal tumors, T-cell lymphoma, testicular cancer, thymoma, thyroid cancer, transitional cell cancer of the renal pelvis and ureter, transitional renal pelvis and ureter cancer, trophoblastic tumors, cell cancer of the renal pelvis and ureter, cancer of the urethra, cancer of the uterus, uterine sarcoma, vaginal cancer, optic pathway and hypothalamic glioma, cancer of the vulva, Waldenstrom's macroglobulinemia, Wilms' tumor and any other hyperproliferative disease, as well as neoplasia, located in the system of a previously mentioned organ.

A "chemotherapy agent," "chemotherapeutic," "anti-cancer agent" or the like, refer to molecules that are recognized to aid in the treatment of a cancer. Contemplated examples include the following molecules or derivatives such as temozolomide, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin and/or lenalidomide or combinations thereof such as cyclophosphamide, methotrexate, 5-fluorouracil (CMF); doxorubicin, cyclophosphamide (AC); mustine, vincristine, procarbazine, prednisolone (MOPP); sdriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

To the extent that chemical structures provided herein are compounds with tautomers by hydrogen migration, a skilled artisan would understand the formula to cover all tautomeric forms.

As used herein, "alkyl" means a noncyclic straight chain or branched, unsaturated or saturated hydrocarbon such as those containing from 1 to 10 carbon atoms, typically 1 to 4 otherwise designated $C_{1-4}$ alkyl. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—$CH_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkylene glycol" refers to an an alkoxy group with a carbon chain of two or more having a terminal hydroxy (i.e., —O—$CH_2CH_2$—OH, —O—$CH_2CH_2CH_2$—OH) or polymers thereof, e.g., polyethylene glycol [—O—$(CH_2CH_2)_n$—OH wherein n is 2 to 10]. In certain embodiments, polyalkylene glycol refers to an alkylene glycol wherein n is 10 to 50, or 10 to 100, or 10 to 500, or 2 to 1,000, or 2 to 5,000, or 100 to 1,000, or 100 to 5,000, or 1,000 to 10,000. Typically polymers are a mixture or distribution of monomers lengths. Thus, in certain embodiments, n is the average number of monomers within a polymer.

"Alkylamino" refers an alkyl group as defined above attached through an amino bridge. An example of an alkylamino is methylamino, (i.e., —NH—$CH_3$).

"Aminoalkyl" refers to an amino group attached through an alkyl bridge as defined above (i.e., $NH_2$-alkyl-).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, and "arylsulfonyl" refers to an aryl attached through a sulfonyl bridge (i.e., —S(=O)$_2$aryl).

"Alkylsulfamoyl" refers to an alkyl as defined above attached through a sulfamoyl bridge (i.e., —NHS(=O)$_2$alkyl), and an "Arylsulfamoyl" refers to an alkyl attached through a sulfamoyl bridge (i.e., —NHS(=O)$_2$aryl).

"Alkylsulfinyl" refers to an alkyl as defined above attached through a sulfinyl bridge (i.e. —S(=O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —$NR_aR_b$, —$NR_aC(=O)R_b$, —$NR_aC(=O)NR_aNR_b$, —$NR_aC(=O)OR_b$, —$NR_aSO_2R_b$, —C(=O)$R_a$, —C(=O) O$R_a$, —C(=O)$NR_aR_b$, —OC(=O)$NR_aR_b$, —O$R_a$, —S$R_a$, —SO$R_a$, —S(=O)$_2R_a$, —OS(=O)$_2R_a$ and —S(=O)$_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Therapeutic Methods

In certain embodiments, this disclosure relates to methods of treating or preventing HvGD comprising administering an effective amount of indole-2-carboxyaldehyde, indole-3-carboxyaldehyde, or derivative to a subject in need thereof. In certain embodiments, this disclosure relates to methods of treating a subject with a hematological malignancy or other cancer comprising transplanting allogenic bone marrow or stem cells in combination with administering an effective amount of an indole-2-carboxyaldehyde, indole-3-carboxyaldehyde, or derivative thereof to a subject in need thereof.

In certain embodiments, this disclosure relates to methods of treating a subject with a hematological malignancy or other cancer comprising administering chemotherapy or radiation or both and transplanting allogenic bone marrow or stem cells in combination with administering an effective amount of an indole-2-carboxyaldehyde, indole-3-carboxyaldehyde, or derivative thereof to a subject in need thereof.

In certain embodiments, this disclosure relates to methods of treating a subject with a hematological malignancy comprising administering a chemotherapy, radiation, or both and transplanting allogenic bone marrow in combination with administering an effective amount of an indole-2-carboxyaldehyde, indole-3-carboxyaldehyde, or derivative thereof to a subject in need thereof.

In certain embodiments, this disclosure relates to methods of treating a subject with a hematological malignancy comprising administering a chemotherapy, radiation, or both and transplanting hematopoietic stem cells in combination with administering an effective amount of an indole-2-carboxyaldehyde, indole-3-carboxyaldehyde, or derivative thereof to a subject in need thereof.

In certain embodiments, the administration of the indole-2-carboxyaldehyde, indole-3-carboxyaldehyde, or derivative is enteral or oral. In certain embodiments, the subject is administered daily doses for more than a week or month. In certain embodiments, the subject is diagnosed with leukemia. In certain embodiments, the subject is diagnosed with lymphoma, multiple myeloma, or myelodysplastic syndromes. In certain embodiments, the subject is a human.

In certain embodiments, the subject is diagnosed with acute myeloid leukemia (AML), chronic myeloid leukemia (CML), acute lymphoblastic leukemia (ALL), Hodgkin lymphoma (relapsed, refractory), non-Hodgkin (relapsed or refractory) lymphoma, neuroblastoma, Ewing sarcoma, a myelodysplastic syndrome, gliomas, solid tumor, thalassemia, aplastic anemia, fanconi anemia, or an immune deficiency syndrome.

For any of the embodiments disclosed herein the indole-2-carboxyaldehyde, indole-3-carboxyaldehyde, or derivative may be administered in combination with an immunosuppressive agent such as glucocorticoids, azathioprine, ciclosporin, tacrolimus, sirolimus, muromonab, basiliximab, or daclizumab.

In certain embodiments, the disclosure relates to treating or preventing intestinal colitis comprising administering an indole-2-carboxyaldehyde, indole-3-carboxyaldehyde, or derivative thereof to a subject in need thereof.

Chemotherapy and radiation therapy typically disproportionately affect rapidly dividing cells. Like cancer cells, bone marrow cells divide more frequently than most cells; thus, chemotherapy treatments also damage the bone marrow cells of a subject. Bone marrow transplantation (BMT) and peripheral blood stem cell transplantation (PBSCT), sometimes referred to as Hematopoietic stem cell transplantation (HSCT), replace stem cells damaged by treatment. In some types of hematological cancers such as leukemia and lymphoma, immune cells from the donor of bone marrow or stem cells target residual cancer cells in the subject that were not destroyed by the chemotherapy and/or radiation therapy.

BMTs are typically more effective when the leukemia or lymphoma is in remission (the signs and symptoms of cancer have disappeared). In certain embodiments, the disclosure contemplates methods disclosed herein wherein methods are performed when leukemia or lymphoma is in remission. BMT and stem cells transplants are also used to treat neuroblastoma (cancer that typically arises in immature nerve cells, e.g., infants and children under 5 years of age) and multiple myeloma.

In certain embodiments, this disclosure relates to methods of treating a subject with neuroblastoma comprising transplanting allogenic bone marrow or stem cells in combination with administering an effective amount of an indole-2-carboxyaldehyde, indole-3-carboxyaldehyde, or derivative thereof to a subject in need thereof.

In certain embodiments, this disclosure relates to methods of treating a subject with a multiple myeloma comprising transplanting allogenic bone marrow or stem cells in combination with administering an effective amount of an indole-2-carboxyaldehyde, indole-3-carboxyaldehyde, or derivative thereof to a subject in need thereof.

The source of restored cells from BMT and stem cell transplantation distinguishes the transplant as autologous transplants, i.e., a subject receive their own stem cells; syngeneic transplants, i.e., a subject receives stem cells from their identical twin; or allogeneic transplants, subjects receive stem cells from their brother, sister, parent, or unrelated donor. In certain embodiments, for any of the methods disclosed herein, the transplant may be autologous, syngeneic or allogeneic.

Graft-versus-Host Disease (GVHD) is an inflammatory disease that is unique to allogeneic transplantation. It is an attack of the "donor" immune cells in the bone marrow against the tissues of the recipient subject. Graft versus tumor effect (GVT) or "graft versus leukemia" effect is the beneficial aspect of the Graft-versus-Host phenomenon. For example, HSCT patients with either acute, or in particular chronic, graft-versus-host disease after an allogeneic transplant tend to have a lower risk of cancer relapse.

In an allogenic bone marrow or peripheral blood hematopoietic stem cell transplant, bone marrow cells or stem cells from a donor are harvested, optionally stored and then engrafted into the patient, typically after the patient receives chemotherapy and/or radiotherapy (conditioning therapy). In the conditioning phase, sufficient doses of chemotherapy and/or radiation are used to eradicate the diseased cells in the bone marrow referred to as myeloablative methods. Treatment kills (ablates) the myeloid stem cells in the bone marrow—the cells that produce new blood cells. Donor stem cells derived from bone marrow or peripheral blood are then infused (engrafted) into the subject. Alternately a reduced intensity conditioning therapy may be used that does not completely destroy the myeloid stem cells, i.e., non-myeloablative transplant. The subject has a period of time with mixed chimerism, i.e., the bone marrow contains both donor and subject cells that theoretically converts to the phenotype of the donor over a sufficient time.

In certain embodiments, the disclosure contemplates administration of indole-2-carboxyaldehyde, indole-3-carboxyaldehyde, or derivative in combination with an autologous or allogenic stem cell transplant. In certain embodiments, for any of the methods disclosed herein the conditioning therapy may be myeloablative or non-myeloablative.

The cells used in BMT come from the liquid center of the bone, referred to as the marrow. After anesthesia, needles are inserted through the skin over the pelvic (hip) bone or, in rare cases, the sternum (breastbone), and into the bone marrow to draw the marrow out of the bone. The harvested bone marrow is typically processed, combined with a preservative, and frozen for cryopreservation.

The hematopoietic stem cells (HSCs or CD34+ cells) used in PBSCT come from the bloodstream typically using an apheresis procedure. The donor may be given a medication to increase the number of stem cells released into the bloodstream. In apheresis, blood is removed through a large vein, e.g., in the arm or a central venous catheter (a flexible tube that is placed in a large vein in the neck, chest, or groin area). The blood goes through a machine that removes the stem cells. The blood is then returned to the donor and the collected cells are stored. The stem cells are then frozen until they are given to the recipient subject.

Agents used to mobilize HSCs include the administration of cytokines with or without chemotherapy agents prior to scheduled collection periods. For example filgrastim and lenograstim are used as single-agent mobilizers. Both agents demonstrate increased concentrations of circulating HSCs. Another method to mobilize HSCs involves the administration of chemotherapy conjunction with cytokines (chemomobilization). Certain chemotherapeutic agents used for chemomobilization include cyclophosphamide and etoposide. During apheresis blood is drawn out of the patient and into a machine and spun in a centrifugation chamber. The centrifugal force separates the red blood cells from other cells due to their high specific weight. Erythrocytes (red blood cells) and polymorphonuclear cells (PMNs) which include neutrophils and eosinophils are generally removed during this fractionation as they denser. Plasma can be separated from peripheral blood mononuclear cells (PBMC) because plasma is less dense. PBMCs include lymphocytes (T cells, B cells, and NK cells), monocytes, and dendritic cells. Further separation of PBMCs can be accomplished by cell selection methods e.g., MACS, fluorescent activated cell sorting, unique RNA expression with molecular beacons.

The CD34 antigen is a common marker for the isolation of hematopoietic stem and progenitor cells. See Kato et al. report the isolation and characterization of CD34+ hematopoietic stem cells from human peripheral blood by high-gradient magnetic cell sorting. Cytometry. 1993, 14(4): 384-92. CD34 also expressed on some lineage-committed cells. Lineage-positive cells may be removed prior to and/or after positive selection of CD34 cells. Magnetic-activated cell sorting (MACS) is a method that allows different cells can be separated positively or negatively with respect to the particular cell surface antigen(s), e.g., CDs. For example, CD34+ peripheral blood progenitor cells (PBPC) may be separated by incubating with magnetic nanoparticles coated with CD34 antibodies. This causes the cells expressing this CD34 to attach to the magnetic nanoparticles. Afterwards the cell solution is transferred on a column placed in a strong magnetic field. In this step, the cells attached to the nanoparticles (expressing the CD34) stay on the column, while other cells (not expressing the antigen) flow through. The CD3 antigen is expressed on T cells and NK cells while the CD19 antigen is expressed on B cells. One can isolate CD3+ and CD19+ cells from PBMC to obtain lymphocytes.

Donor lymphocyte infusion (DLI) is a form of adoptive immunotherapy may be performed after hematopoietic stem cell transplantation. Lymphocytes from the original stem cell donor are infused, e.g., after the transplant, to augment an anti-tumor immune response. Donated lymphocytes contain T cells of the immune system that can recognize and destroy cancer cells. In certain embodiments, for any of the methods disclosed herein the subject has a hematopoietic stem cell transplantation from the donor in combination with administration or transplantation of donor lymphocytes, i.e., a donor lymphocyte infusion.

In certain embodiments, the disclosure contemplates administration of indole-2-carboxyaldehyde, indole-3-carboxyaldehyde, or derivative in combination with an autologous or allogenic stem cell transplant in conjunction with cytotoxic T cells, e.g., genetically modified cytotoxic T cells that express chimeric CD19 receptors such as CTL019 cells. Chimeric antigen receptors are genetically engineered receptors that couple a single-chain Fv domain to intracellular T-cell signaling domains of the T-cell receptor, thereby redirecting cytotoxic T lymphocytes to cells expressing single-chain Fv domain. With the use of lentiviral-vector technology for gene transfer and permanent T-cell modification, CTL019 (also known as CART19)-engineered T cells express a chimeric antigen receptor in which the T-cell activation signal is provided by the CD3-zeta domain, and the costimulatory signal is provided by the CD137 (4-1BB) domain. See Garfall et al., Chimeric Antigen Receptor T Cells against CD19 for Multiple Myeloma, 2015, N Engl J Med, 373(11):1040-7.

Indole Derivatives

In certain embodiments, indole-3-carboxyaldehyde derivatives are compounds having formula I, esters, or salts thereof, wherein;

A is N or $CR^4$; B is N or $CR^5$, D is N or $CR^6$; E is N or $CR^7$;

$R^1$, $R^2$, $R^3$, $R^4$, $R^5$, $R^6$, and $R^7$ are each individually and independently, hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkyl sulfonyl, aryl sulfonyl, carbocyclyl, aryl, or heterocyclyl, wherein $R^1$, $R^2$, $R^3$, $R^4$, $R^5$, $R^6$, and $R^7$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, 2-methoxyethoxy, 2-ethoxyethoxy, acetyl, acetoxy, methylamino, ethylamino, dimethylamino, diethylamino, N-methyl-N-ethylamino, acetylamino, N-methylcarbamoyl, N-ethyl carbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethylsulfamoyl, N,N-di ethyl sulfamoyl, N-methyl-N-ethylsulfamoyl, carbocyclyl, aryl, or heterocyclyl.

In certain embodiments, indole-2-carboxyaldehyde derivatives are compounds having formula I, esters, or salts thereof, wherein;

A is N or CR$^4$; B is N or CR$^5$, D is N or CR$^6$; E is N or CR$^7$;

$R^1$, $R^2$, $R^3$, $R^4$, $R^5$, $R^6$, and $R^7$ are each individually and independently, hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkyl sulfinyl, alkyl sulfonyl, aryl sulfonyl, carbocyclyl, aryl, or heterocyclyl, wherein $R^1$, $R^2$, $R^3$, $R^4$, $R^5$, $R^6$, and $R^7$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, 2-methoxyethoxy, 2-ethoxyethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-dimethylsulfamoyl, N-methyl-N-ethylsulfamoyl, carbocyclyl, aryl, or heterocyclyl.

Formulations

Pharmaceutical compositions comprising indole-3-carboxaldehyde or derivatives disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se.

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778; 6,369,086; 6,369,087; and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more compounds can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions. Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the compound(s) to carrier and/or other substances may vary from about 0.5 to about 100 wt % (weight percent). For oral use, the pharmaceutical formulation will generally contain from about 5 to about 100% by weight of the active material. For other uses, the pharmaceutical formulation will generally have from about 0.5 to about 50 wt % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., Nox inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compounds described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the compounds can be administered in the same dosage form or in separate dosage forms with one or more other active agents.

Pharmaceutical compositions of the compounds of this application, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride or sodium citrate, may also be added.

Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols or water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax. The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation may be in the form of a syrup, elixir, emulsion, or an aqueous or non-aqueous suspension. Such a liquid formulation may be administered directly or filled into a soft gelatin capsule.

The pharmaceutical compositions of the application may be in the form of a sterile injectable preparation. Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents.

Microbiota Factors that Regulate Host Sensitivity to Deleterious Immune Responses In organisms as diverse as *C. elegans* and mammals, the capacity of intestinal cells to maintain barrier integrity is critical to survival from various stressors. Data suggest that indoles, which are produced by commensal organisms, regulate sensitivity of the barrier to damage by stressors, and in higher organisms, additionally regulate the capacity to repair barrier breaches and to modulate immune tolerance. Indoles function as hormones in plants. *C. elegans* and other nematodes live in constant contact with both plants and bacteria, and it may be that indoles serve as intermediaries of signaling. Molecular detectors and effectors of indole signaling are both ancient (>500M years old) and conserved, at least between invertebrates and vertebrates.

The microbiota is increasingly becoming recognized for its role in exacerbating or limiting human disease, including that caused by pathogen infection and inflammation. Fecal transplants have recently been used to reset imbalances in the microbiota, thereby limiting susceptibility to infection caused by the intestinal pathogens such as *C. difficile*, or, alternatively, to inflammatory colitis. A limitation of fecal transplants, however, is that the transplanted bacteria cannot necessarily displace extant flora. Additionally, fecal transplants cannot safely be done on patients with colitis, because the procedure itself can further damage and inflamed colon and cause sepsis. An alternative is to identify molecules secreted by the microbiota, and administer those molecules as drugs, thereby achieving the same effect as a fecal transplant. The problem is how to identify important molecules secreted by the microbiota. Secreted molecules were purified from commensal strains of *E. coli* that reduce susceptibility to lethal intestinal damage caused by various stressors in the nematode *Caenorhabditis elegans*. These molecules also appear to confer resistance to damage caused by stressors in the fruit fly *Drosophila melanogaster*. Whether indole-3-carboxaldehyde (ICA), could limit susceptibility of mice to immune-mediated damage was tested. ICA protected mice from intestinal damage caused by transplanted allogeneic T cells in a model of Graft vs. Host Disease (GvHD). ICA also altered immune tolerance such that allogeneic T cells no longer responded to allo-antigens. Finally, ICA conferred 90% survival on mice with transplanted allogeneic T cells compared to untreated animals, which all succumbed to GvHD. Using genetic methods, a putative receptor and signaling pathway was defined by which ICA confers damage tolerance in *C. elegans*. ICA can also suppress GvHD, yet permit transplanted T cells to still recognize deleterious antigens outside the intestinal tract (e.g. those on leukemic cells). In summary, molecules secreted by commensal bacteria alter susceptibility of intestinal epithelia to damage and mitigate deleterious immune responses, also preserve those that can attack aberrant cells including cancer.

ICA mediates protection in a murine model of Graft vs. Host Disease (GvHD), in which transplanted allogeneic T cells attack the host, causing lethal colitis and sepsis. Because the predominant protective effect of ICA is on intestinal barrier integrity, the approach, while suppressing GvHD, still allows transplanted T cells to retain activity against, for example, leukemic cells (so called Graft vs. Leukemia; GvL).

EXPERIMENTAL

Administration of a Tryptophan Metabolite, Indole-3-carboxaldehyde, Reduces Graft Versus Host Disease A tryptophan metabolite, indole-3-carboxaldehyde (ICA), was identified to prevent lethal GvHD and allows normal engraftment by allogeneic donor bone marrow when fed to transplant recipients for the first few weeks after transplant. Lethally irradiated B10.BR (H2k) mice were transplanted with $3 \times 10^6$ T cell depleted bone marrow cells (TCD-BM) alone or the combination of TCD-BM plus $2 \times 10^6$ purified T cells from B6 (H2b) donor mice. Mice received daily gavage with 100 mg/kg or 150 mg/kg ICA or vehicle through day 38 post-transplant. Survival and clinical manifestations of GvHD were monitored through day 62. Histopathology of the gut, cytokines in serum and colon homogenates, intracellular cytokine staining of donor T-cells and bacterial counts in mesenteric lymph nodes (using blood agar plates) were measured in a separate cohort of experimental mice euthanized on day 20. Additionally, a secondary transplant was conducted to test the allo-proliferative capacity (in vivo CFSE dilution assay) and GvHD activity of T-cells from spleens of mice in the TCD-BM+T cells+150 mg/kg ICA group that survived to day 62, compared to B6 T cells, in combination with fresh B6 TCD-BM, in B10.BR recipients.

Figure 1:
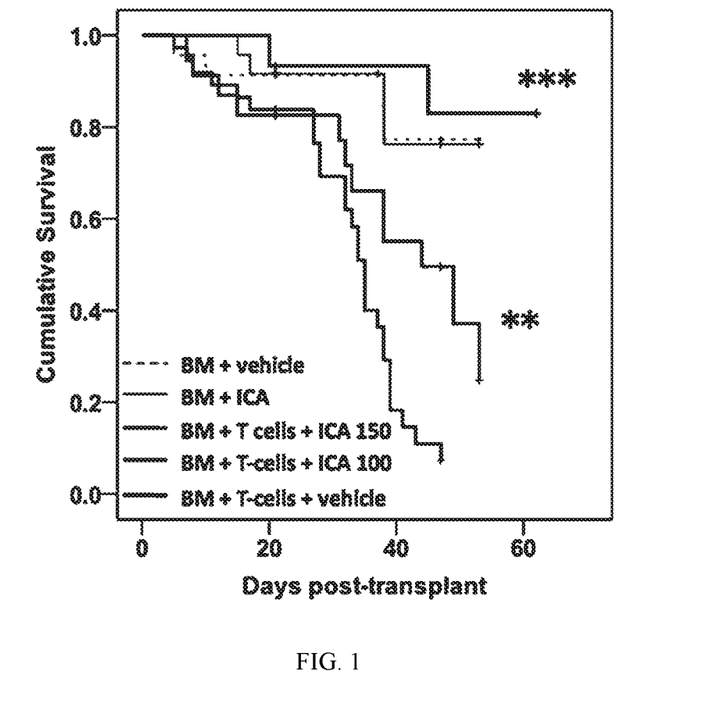
Figure 2:
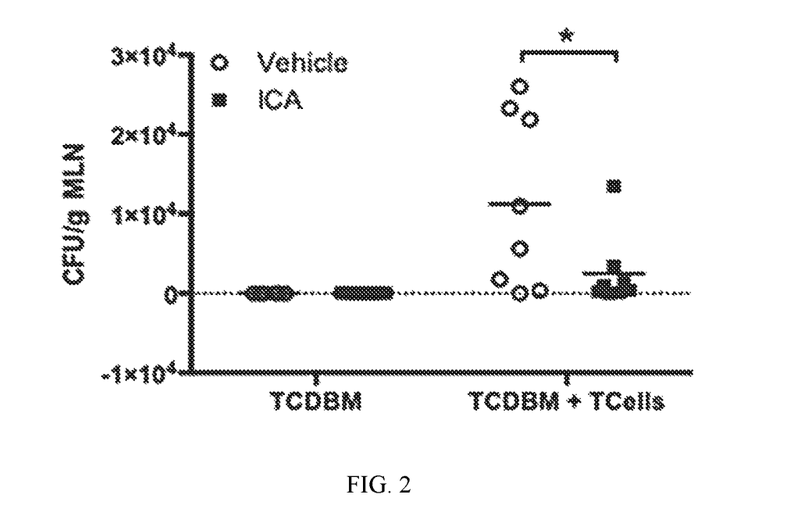

Survival curves for mice transplanted with TCD-BM+T-cells are shown in FIG. 1. They were fed vehicle, 100 mg/kg/day of ICA, or 150 mg/kg/day of ICA by oral gavage. Only 7% of the recipients of TCD-BM+T cells treated with vehicle only survived to day 46. ICA administration improved survival in a dose-dependent manner: recipients given 100 mg/kg/day of ICA had 20% survival at day 52 (p=0.009) and administration of 150 mg/kg/day of ICA resulted in 83% survival of recipients of TCD-BM+T cells (*p<0.001). ICA was well tolerated without serious toxicity in recipients of BM grafts without GvHD-causing T-cells. ICA-treated recipients of TCD-BM+T cells had improved thymopoiesis and decreased levels of inflammatory cytokines. Histological analysis of colonic tissue from these ICA-treated recipients also showed marked reduction of GvHD pathology and decreased bacterial colonization of mesenteric lymph nodes (MLN) compared to vehicle-treated control animals (FIG. 2, *p<0.01), indicating enhanced gastrointestinal barrier function. T cells recovered from ICA-treated TCD-BM+T cell transplant recipients at day 62 had been rendered tolerant to recipient type alloantigens in secondary transplant in vivo assays as shown by reduced proliferation of CFSE-stained T cells and lack of GvHD activity in secondary B10.BR recipients.

These data indicate that enteral administration of ICA causes a dramatic reduction of GvHD in a MHC mismatched model of allogeneic bone marrow transplantation. It may be that this effect is mediated through activation of the aryl hydrocarbon receptor in innate lymphoid cells in the lamina propria of the gut, stimulating regeneration of the gut epithelium and reducing trans-epithelial migration of gut bacteria that contribute to GvHD. Further development and exploration of the mechanism by which ICA treatment reduces GvHD could have a major impact on improving the safety of allogeneic bone marrow transplantation, and increase the availability of donors for those patients who currently lack an HLA matched sibling or volunteer donor.

ICA Inhibits Infectious Colitis in Mice

Figure 3A:
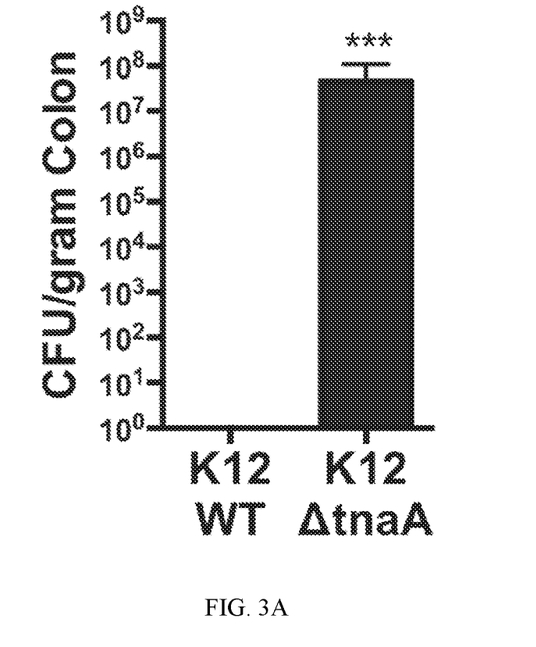
Figure 3B:
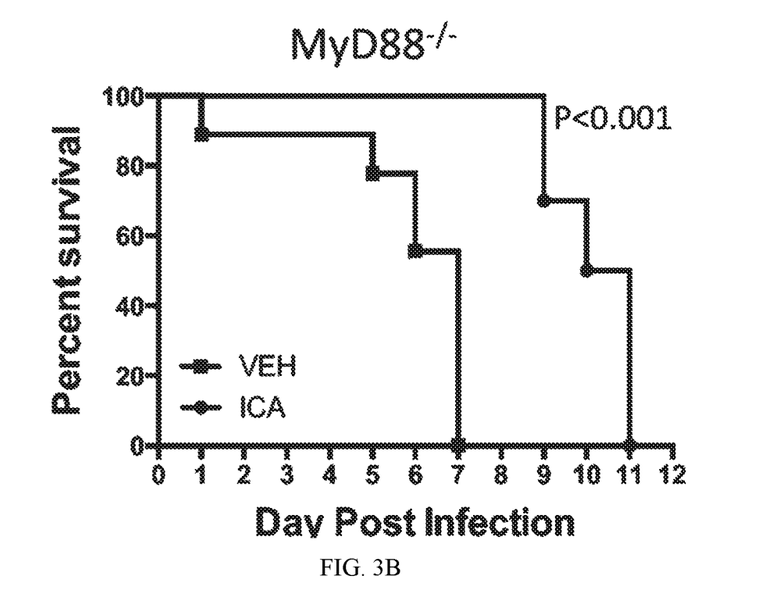

Indoles were assessed in models of epithelial barrier integrity and immune regulation in mammals. Pathogenic *E. coli* (EPEC and EHEC) and the related mouse pathogen *C. rodentium* encode virulence factors and a Type III secretion system through the LEE pathogenicity island, and cause diarrhea and colitis. In vivo, *C. rodentium* causes infectious colitis, characterized by neutrophil and T cell infiltration into the lamina propria, transient increases in IL-22, epithelial barrier breakdown, crypt hyperplasia (an indicator of repair), and dissemination of bacteria throughout the body. Colonizing mice with K12 suppressed a subsequent *C. rodentium* infection better than colonizing with K12Δ, a mutant that does not make ICA (FIG. 3A). Thus, indole derivatives, produced via commensal *E. coli* TnaA, mitigate pathogen infection. ICA was administered to mice that were infected with *C. rodentium*. ICA maintained barrier integrity and prolonged survival (FIG. 3B).

ICA Protects Against Non-infectious Immune- and Radiation-mediated Intestinal Damage.

Allogeneic hematopoietic stem cell transplantation (HSCT) is a potentially curative treatment for a number of malignant and non-malignant hematologic conditions. Severe acute graft-versus-host disease (GvHD) remains a major barrier to allogeneic HSCT, complicating approximately 20% of all transplant. The pathogenesis of acute GvHD has been summarized in three sequential phases: 1) activation of antigen-presenting cells (APCs); 2) donor T cell activation, proliferation, differentiation, and migration; and 3) target tissue destruction. Injury to the gastrointestinal tract is especially important to this process as barrier breach allows for additional inflammatory stimuli (e.g. LPS) to further enhance activation of APCs. The rapid trafficking of donor lymphocytes to secondary lymphoid organs and then into target organs is presumed to be responsible for the clinical manifestations of acute GvHD, which primarily occurs in 3 organ systems: skin, gut and liver. Prophylactic immunosuppression can limit the incidence and severity of GvHD, but increases the risk of opportunistic infections and relapse. Once established, GvHD can be difficult to treat with only one third of patients responding to initial steroid therapy. Thus, novel means to prevent GvHD are urgently needed.

Figure 4A:
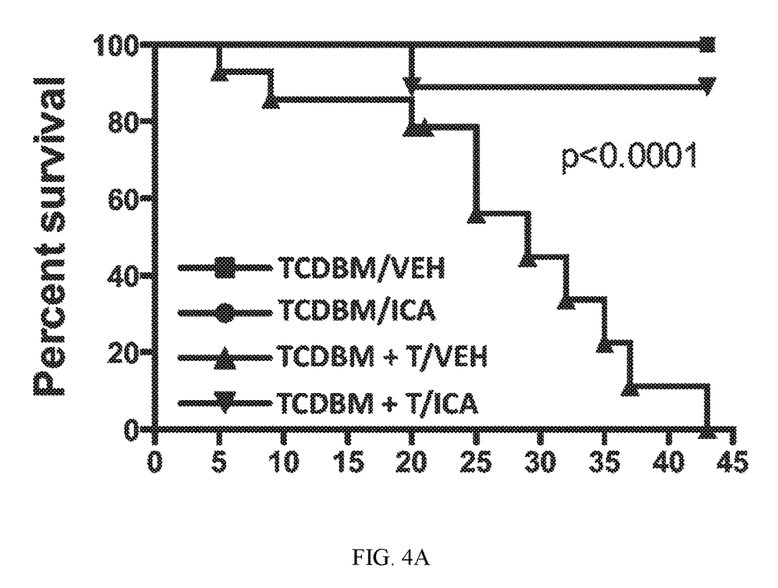
FIG. 4A shows survival curves of ICA on GvHD. B6,B10.BR allo MHC mismatched transplants, administering $3 \times 10^6$ MHC mismatched donor T cells following myeloablative irradiation with 11Gy that injures gut epithelia. Control groups with allogeneic T cell depleted BM transplants do not develop GvHD. ICA (150 mg/kg/d) p.o. QD.
Figure 4B:
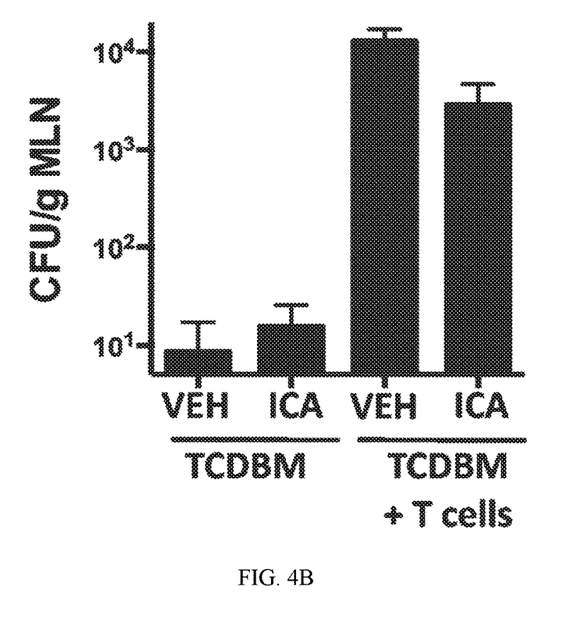
FIG. 4B shows data on CFU of bacterial disseminating to mesenteric lymph nodes.

The gut microbiota contribute to GvHD, yet some *Lactobacillus* species, which produce ICA and related molecules, mitigate GvHD. Thus, depending on the composition of the microbiota, molecules derived from it might protect from GvHD or exacerbate it. ICA might limit GvHD, by regulating barrier integrity. A myeloablative dose of total body irradiation (TBI) (11Gy) was administered to B10.BR mice, an established murine model of GvHD, in which followed by transplantation of T cell depleted bone marrow (TCDBM) plus/or minus 3×10$^6$ allo-MHC mismatched T cells all from donor C57Bl/6 mice. Mice administered TCDBM+T cells consistently developed GvHD, increased apoptosis and crypt hyperplasia in the colon (e.g. FIG. 4C), bacterial dissemination to mesenteric lymph nodes (FIG. 4B), increased Th17 responses, and 90% lethality by 30 days (FIG. 4A). Control mice, receiving TCDBM only, did not develop disease. Administration of ICA (p.o., 150 mg/kg QD) not only abrogated bacterial dissemination (FIG. 4B) and colon damage (FIG. 4C), but also prevented weight loss and death in 90% of animals receiving TCDBM+T cells.

Thus, ICA protects against GvHD. Importantly, ICA predominantly affected gastrointestinal GvHD, but was without effect on liver GvHD.

Figure 5A:
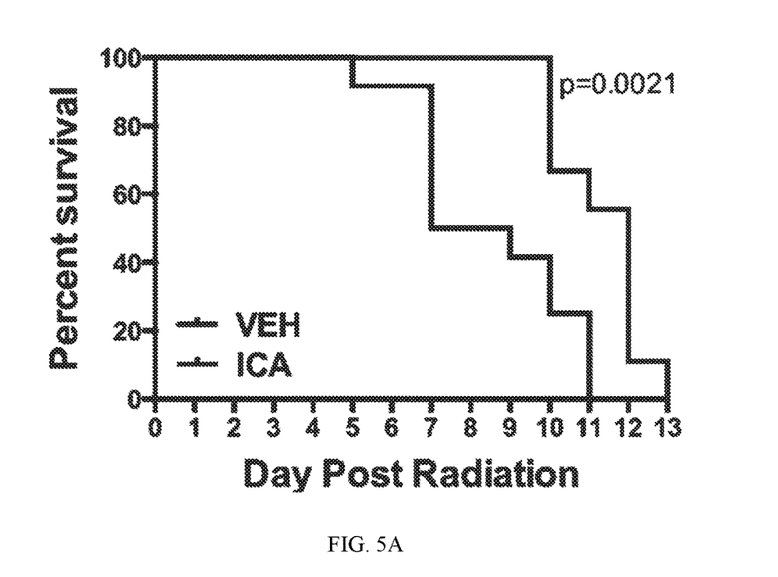
FIG. 5A shows data on the effects of ICA on Radiation enteritis indicating ICA promotes survival from radiation (no BM transplant).
Figure 5B:
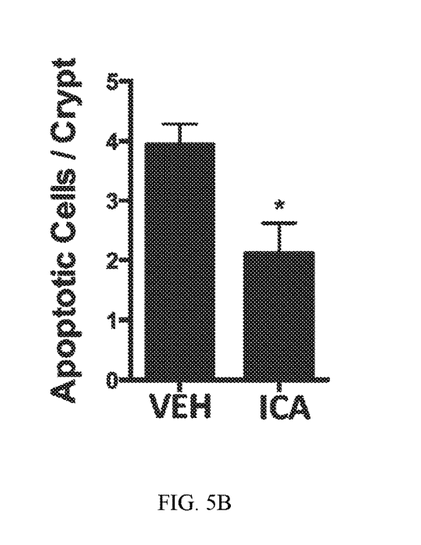
FIG. 5B shows data indication apoptotic cells decrease with ICA.
Figure 5C:
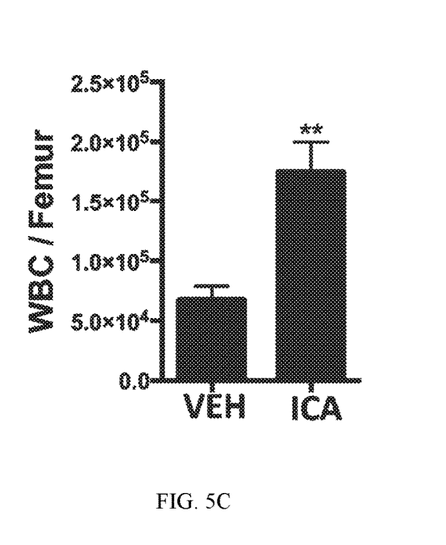
FIG. 5C shows data indicating ICA enhances survival of hematopoietic progenitors in the BM.

Mice were subjected to 12Gy TBI without BM transplant, a lethal model in which most animals succumb to radiation-induced enteritis by about 7 days post-irradiation (p.i.), as opposed to hematopoietic failure at about 14 days p.i. Significantly, ICA treatment extended mean survival time from 7 days to 12 days p.i., with all ICA treated animals surviving 10 to 13 days p.i., a timeframe indicative of death due to hematopoietic failure rather than colitis (FIG. 5A). Accordingly, ICA-treated animals had fewer apoptotic cells in the colon at 6 hr p.i. (FIG. 5B), and increased numbers hematopoietic cells in the marrow at 4 days p.i. (FIG. 5C). Thus, ICA reduced the death rate of both colonic and hematopoietic stem cells. Together, these data suggest that ICA not only reduced epithelial damage, but also stimulated repair. While reduced intestinal damage and improved repair likely accounts at least in part for initial improvement in GvHD animals, additional effects on immune tolerance were also evident, but only over very long periods of administration (>3 months). After long-term treatment (50 days), ICA makes donor C57Bl/6 T cells irreversibly and permanently tolerant to B10.BR antigens. However, these T cells remain responsive to allo-antigens other than B10.BR or C57Bl/6 upon secondary transplantation.

The invention claimed is:

1. A method of treating a subject with a hematological malignancy comprising transplanting allogenic bone marrow in combination with administering an effective amount of an indole-2-carboxyaldehyde, indole-3-carboxyaldehyde, or derivative thereof to a subject in need thereof, wherein the derivative is a compound having formula I, esters, or salts thereof, wherein;

A is N or CR$^4$; B is N or CR$^5$, D is N or CR$^6$; E is N or CR$^7$;

R$^1$, R$^2$, R$^3$, R$^4$, R$^5$, R$^6$, and R$^7$ are each, individually and independently, hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkyl sulfonyl, aryl sulfonyl, carbocyclyl, aryl, or heterocyclyl, wherein R$^1$, R$^2$, R$^3$, R$^4$, R$^5$, R$^6$, and R$^7$ are optionally substituted with one or more, the same or different, R$^{10}$, R$^{10}$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein R$^{10}$ is optionally substituted with one or more, the same or different, R$^{11}$;

R$^{11}$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, 2-methoxyethoxy, 2-ethoxyethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The method of claim 1, wherein the administration is enteral.

3. The method of claim 1, wherein the subject is administered a daily dose for more than a week or month.

4. The method of claim 1, wherein the subject is diagnosed with leukemia.

5. The method of claim 1, wherein the subject is diagnosed with lymphoma, multiple myeloma, or myelodysplastic syndromes.

6. The method of claim 1, wherein the subject is a human.

7. A method of treating a subject with a hematological malignancy comprising providing a conditioning regimen and administering an effective amount of an indole-2-carboxyaldehyde, indole-3-carboxyaldehyde, or derivative thereof to a subject in need thereof, wherein the derivative is a compound having formula I, esters, or salts thereof, wherein;

A is N or $CR^4$; B is N or $CR^5$, D is N or $CR^6$; E is N or $CR^7$;

$R^1$, $R^2$, $R^3$, $R^4$, $R^5$, $R^6$, and $R^7$ are each, individually and independently, hydrogen, alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkyl sulfonyl, aryl sulfonyl, carbocyclyl, aryl, or heterocyclyl, wherein $R^1$, $R^2$, $R^3$, $R^4$, $R^5$, $R^6$, and $R^7$ are optionally substituted with one or more, the same or different, $R^{10}$;

$R^{10}$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylene glycol, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$, and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, 2-methoxyethoxy, 2-ethoxyethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

8. The method of claim 7, wherein the conditioning regimen is a myelosuppressive or myeloablative doses of chemotherapy.

9. The method of claim 7, wherein the conditioning regimen comprises administering busulfan, melphalan, fludarabine, cyclophosphamide, etoposide, thioTEPA, or combinations thereof.

10. The method of claim 7, wherein the conditioning regimen is doses of ionizing radiation.

* * * * *